US007488758B2

(12) United States Patent
Merli et al.

(10) Patent No.: US 7,488,758 B2
(45) Date of Patent: Feb. 10, 2009

(54) LEVALBUTEROL HYDROCHLORIDE POLYMORPH B

(75) Inventors: Valeriano Merli, Lecco (IT); Silvia Mantovani, Lendinara (IT); Stefano Bianchi, Como (IT); Paola Daverio, Milan (IT); Angelo Spreafico, Lecco (IT); Judith Aronhime, Rehovot (IL); Adrienne Kovacsne-Mezei, Debrecen (HU)

(73) Assignee: Teva Pharmaceutical Fine Chemicals, S.r.l., Bulciago (LC) (IT)

( * ) Notice: Subject to any disclaimer, the term of this patent is extended or adjusted under 35 U.S.C. 154(b) by 449 days.

(21) Appl. No.: 11/133,722

(22) Filed: May 20, 2005

(65) Prior Publication Data

US 2005/0267216 A1 Dec. 1, 2005

Related U.S. Application Data

(60) Provisional application No. 60/573,025, filed on May 20, 2004, provisional application No. 60/577,979, filed on Jun. 7, 2004, provisional application No. 60/577,819, filed on Jun. 7, 2004, provisional application No. 60/583,777, filed on Jun. 28, 2004, provisional application No. 60/583,642, filed on Jun. 28, 2004, provisional application No. 60/587,673, filed on Jul. 13, 2004, provisional application No. 60/632,625, filed on Dec. 2, 2004, provisional application No. 60/646,803, filed on Jan. 25, 2005.

(51) Int. Cl.
*A61K 31/135* (2006.01)
*C07C 211/00* (2006.01)

(52) U.S. Cl. .................. 514/646; 564/305; 564/336

(58) Field of Classification Search .............. 564/305, 564/336; 514/646
See application file for complete search history.

(56) References Cited

U.S. PATENT DOCUMENTS

| 5,399,765 | A | * | 3/1995 | Gao et al. ................. 564/365 |
| 5,442,118 | A | | 8/1995 | Gao et al. |
| 5,545,745 | A | * | 8/1996 | Gao et al. ................. 560/42 |
| 6,365,756 | B1 | | 4/2002 | Stevens et al. |

FOREIGN PATENT DOCUMENTS

| AU | B-25559/95 | 12/1995 |
| CA | 1 040 658 | 10/1978 |
| CA | 2 190 577 | 11/1995 |
| CA | 2 320 756 | 8/1999 |
| CN | 1273966 A | 11/2000 |
| CN | 1382685 | 12/2002 |
| GB | 1 298 494 | 12/1972 |
| GB | 1298494 | 12/1972 |
| WO | WO 92/04314 | 3/1992 |
| WO | WO 95/29146 | 11/1995 |
| WO | WO 95/32178 | 11/1995 |
| WO | WO 99/42460 | 8/1999 |
| WO | WO 02/48090 A1 | 6/2002 |
| ZA | 990977 | 4/2000 |

OTHER PUBLICATIONS

"Briefing: Levalbuterol Hydrochloride; Levalbuterol Inhalation Solution" 2006 USPC, Inc. 33(1) In-Process Revision: Levalbuterol Hydrochloride http://www.usppf.com/pf/pub/data/v331/MON_IPR_331_m44602.xml, pp. 1-6.
Handley, D.A., et al., "Levalbuterol hydrochloride", Exp. Opin. Invest. Drugs, 1998, 7(12), pp. 2027-2041.
Halabi, A., et al., "Validation of a chiral HPLC assay for (R)-salbutamol sulfate", Journal of Pharmaceutical and Biomedical Analysis, 2004, 34, pp. 45-51,.
Ferrayoli, C.G., et al., "Resolution of Racemic Albuterol Via Diastereomeric Salts Formation with Di-*p*-Toluoyl-D-Tartaric Acid", Enantiomer, 2000, 5, pp. 289-291.
Caira, M.R., "Crystalline Polymorphism of Organic Compounds", Topics in Current Chemistry, 1998, 198, pp. 163-208.

* cited by examiner

*Primary Examiner*—Rei-Tsang Shiao
*Assistant Examiner*—Susannah Chung
(74) *Attorney, Agent, or Firm*—Kenyon & Kenyon LLP

(57) ABSTRACT

The invention is directed to levalbuterol HCl Form B and methods of making the same.

15 Claims, 4 Drawing Sheets

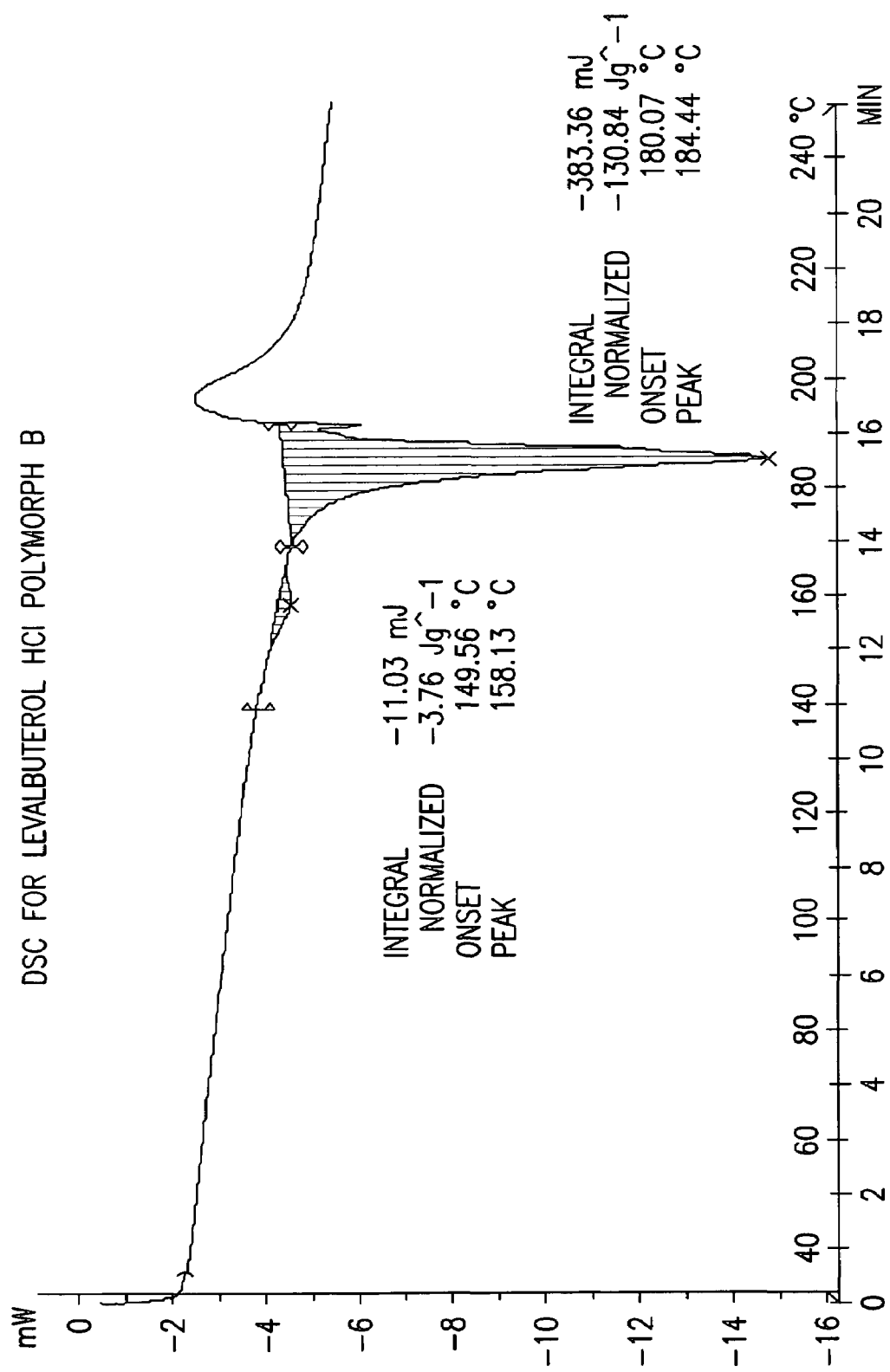

LEVALBUTEROL HYDROCHLORIDE POLYMORPH B

CROSS-REFERENCE TO RELATED APPLICATIONS

This application claims the benefits of U.S. Provisional Patent Application Nos. 60/573,025, filed May 20, 2004, 60/577,979, filed Jun. 7, 2004, 60/646,803, filed Jan. 25, 2005, 60/577,819, filed Jun. 7, 2004, 60/583,777, filed Jun. 28, 2004, 60/583,642, filed Jun. 28, 2004, 60/587,673, filed Jul. 13, 2004 and 60/632,625, filed Dec. 2, 2004, the contents of all of which are incorporated herein by reference.

FIELD OF THE INVENTION

The present invention encompasses levalbuterol hydrochloride polymorph B and processes for the preparation thereof.

BACKGROUND OF THE INVENTION

Activation of $\beta_2$-adrenergic receptors on airway smooth muscle leads to the activation of adenylcyclase and to an increase in the intracellular concentration of cyclic-3',5'-adenosine monophosphate (cyclic AMP). This increase in cyclic AMP leads to the activation of protein kinase A, which inhibits the phosphorylation of myosin and lowers intracellular ionic calcium concentrations, resulting in relaxation. Levalbuterol relaxes the smooth muscles of the airways from the trachea to the terminal bronchioles. Levalbuterol acts as a functional antagonist to relax the airway irrespective of the spasmogen involved, thus protecting against all bronchoconstrictor challenges. Increased cyclic AMP concentrations are also associated with the inhibition of release of mediators from mast cells in the airway. The chemical name for levalbuterol HCl is (R)-$\alpha^1$-[[(1,1-dimethylethyl)amino]methyl]-4-hydroxy-1,3-benzenedimethanol hydrochloride.

Levalbuterol HCl has been synthesized using a variety of synthetic schemes. For example, Great Britain patent No. 1298494 discloses synthesizing levalbuterol first by crystallizing the alkyl acetate of the 4-carboxylate derivative (Formula 1) using ditolyltartaric acid and isolating the selected crystalline fraction.

Formula 1

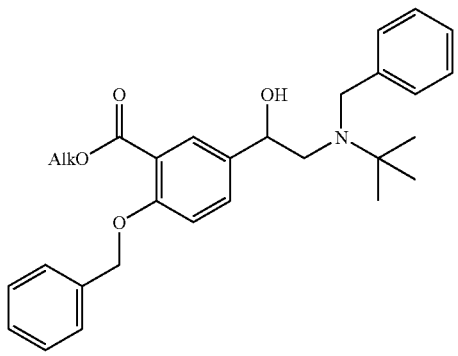

Thereafter, the crystal undergoes debenzylation deprotection, followed by ester reduction to yield levalbuterol.

In Chinese patent No. 1,273,966, the salt of (R)-albuterol D-dibenzoyltartaric acid is treated with potassium carbonate in water and an organic solvent, such as ethylacetate. After phase separation and extraction of the aqueous layer, the collected organic layer is dried and levalbuterol free base crystallizes overnight. The crystalline levalbuterol free base is dissolved in anhydrous alcohol, followed by addition of HCl to obtain crystalline levalbuterol HCl. Also, levalbuterol HCl is synthesized by acid displacement from (R)-albuterol D-dibenzoyltartaric acid salt suspended in acetone and the addition of an ether solution of HCl.

Despite the many attempts of the prior art to synthesize enantiomerically pure levalbuterol, still novel synthetic processes for preparing polymorphically pure levalbuterol HCl are needed to reduce the steps necessary for synthesis and purification without sacrificing compound purity.

SUMMARY OF THE INVENTION

On embodiment of the invention encompasses levalbuterol hydrochloride Form B characterized by at least one of x-ray diffraction by peaks at 8.7, 14.5, 19.0, and 19.6 degree two-theta, ±0.2 degree two-theta; IR peaks at 2970, 2802, 1615, 1599, 1560, 1546, 1507, 1482, 1444, 1364, 1313, 1199, 1151, 1111, 1094, 1034, 992, 829, 697, 653, 597, 537, and 454 cm$^{-1}$; or DSC curves of small endothermic event in the temperature range of 144° C. to 169° C. and decomposes during melting in the temperature range of 181° C. to 188° C. The levalbuterol hydrochloride Form B may be further characterized by x-ray diffraction peaks at 20.6, 22.6, 30.9, and 35.0 degree two-theta, ±0.2 degree two-theta. The levalbuterol hydrochloride Form B may be further characterized by infrared peaks at 3137, 2865, 2437, 2364, 1268, and 1071 cm$^{-1}$. Another embodiment of the invention encompasses levalbuterol hydrochloride Polymorph B in about 98% purity as determined by HPLC.

Another embodiment of the invention encompasses processes for preparing levalbuterol HCl Polymorph B comprising suspending (R)-SLB(D)-DBTA ((R)(-)-$\alpha^1$-[[(1,1-dimethylethyl)amino]methyl]-4-hydroxy-1,3-benzenedimethanol-(D)-di-benzoyltartrate) in at least one solvent; adding HCl in a $C_1$-$C_4$ alcohol to the suspension of the solid (R)-SLB(D)-DBTA until levalbuterol HCl Polymorph B is obtained; and isolating the levalbuterol HCl Polymorph B. The solvent includes at least one linear or branched $C_3$-$C_{10}$ ester, linear or branched $C_3$-$C_{10}$ ketone, linear or branched $C_3$-$C_{10}$ ether, $C_6$-$C_{10}$ aromatic hydrocarbon, or linear or branched $C_1$-$C_4$ alcohol.

Preferably, the solvent comprises 95% ethylacetate and about 5% methanol by volume.

BRIEF DESCRIPTION OF THE DRAWINGS

FIG. 4 is a characteristic DSC curve of levalbuterol HCl Polymorph B.

DETAILED DESCRIPTION OF THE INVENTION

Figure 1:
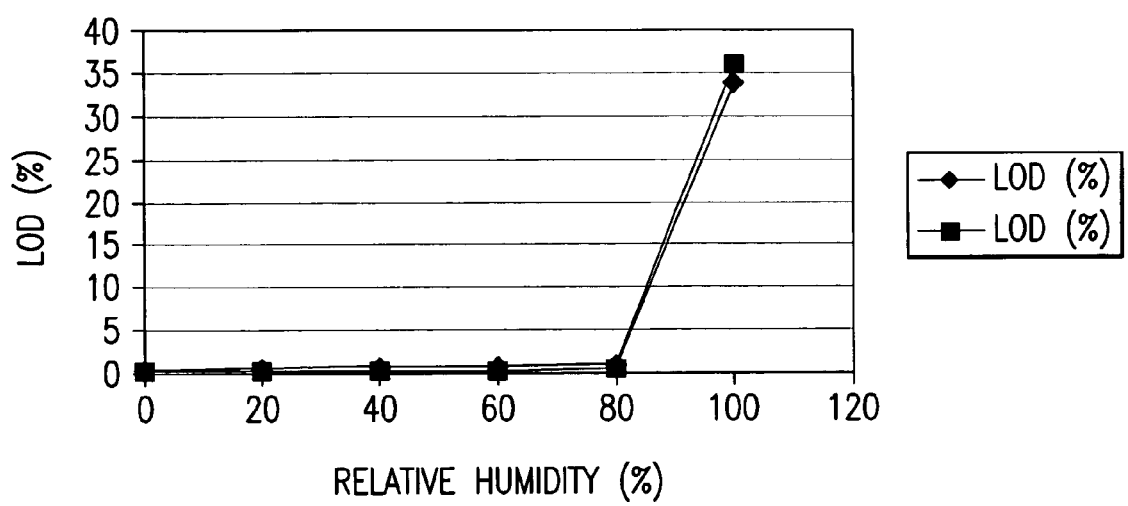
FIG. 1 illustrates the hygroscopicity levels of levalbuterol HCl Polymorph A and Polymorph B after a one-week exposure to various percentages of relative humidity.
Figure 2:
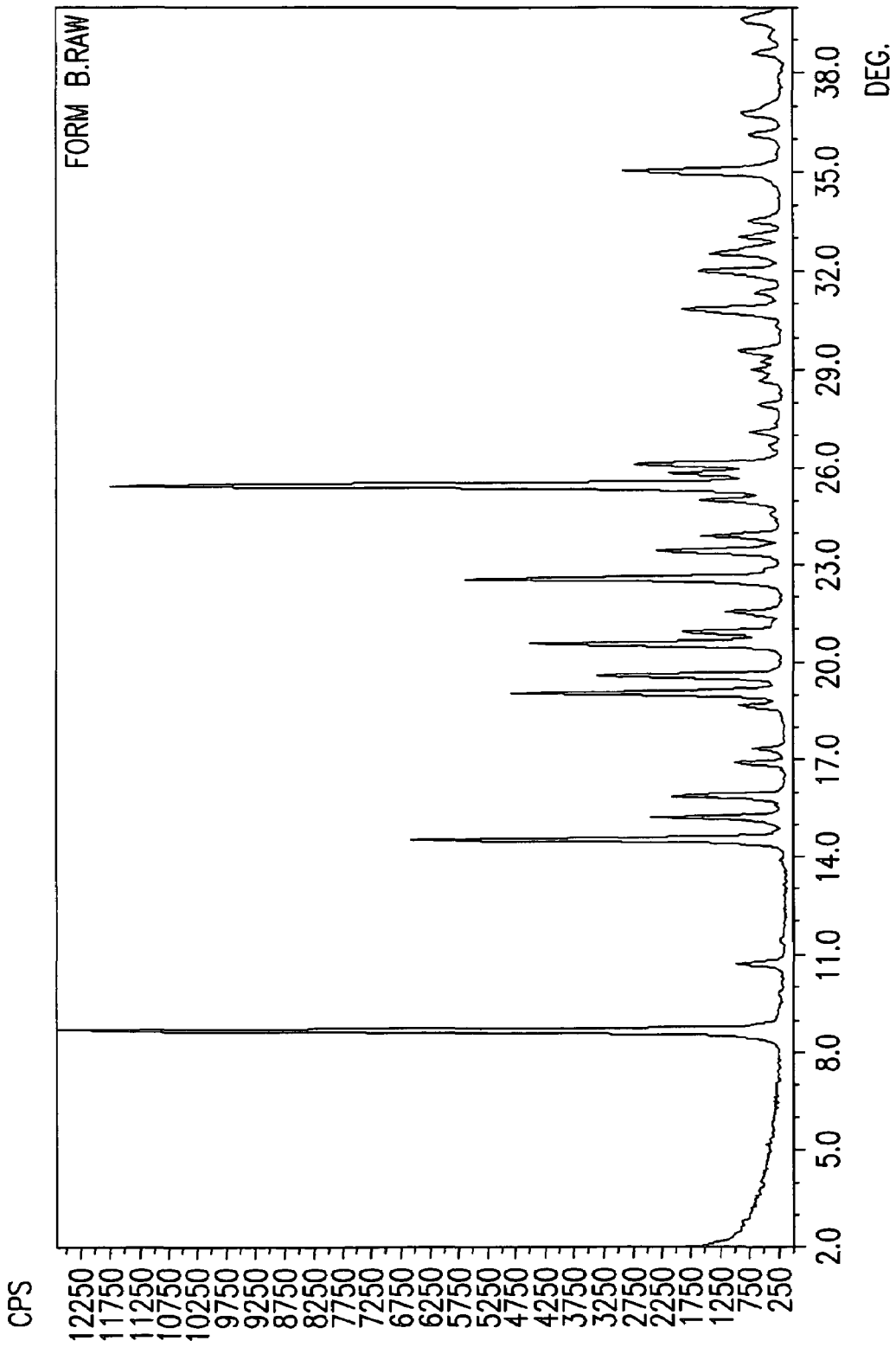
FIG. 2 is a characteristic powder X-ray diffraction pattern of levalbuterol HCl Polymorph B.
Figure 3:
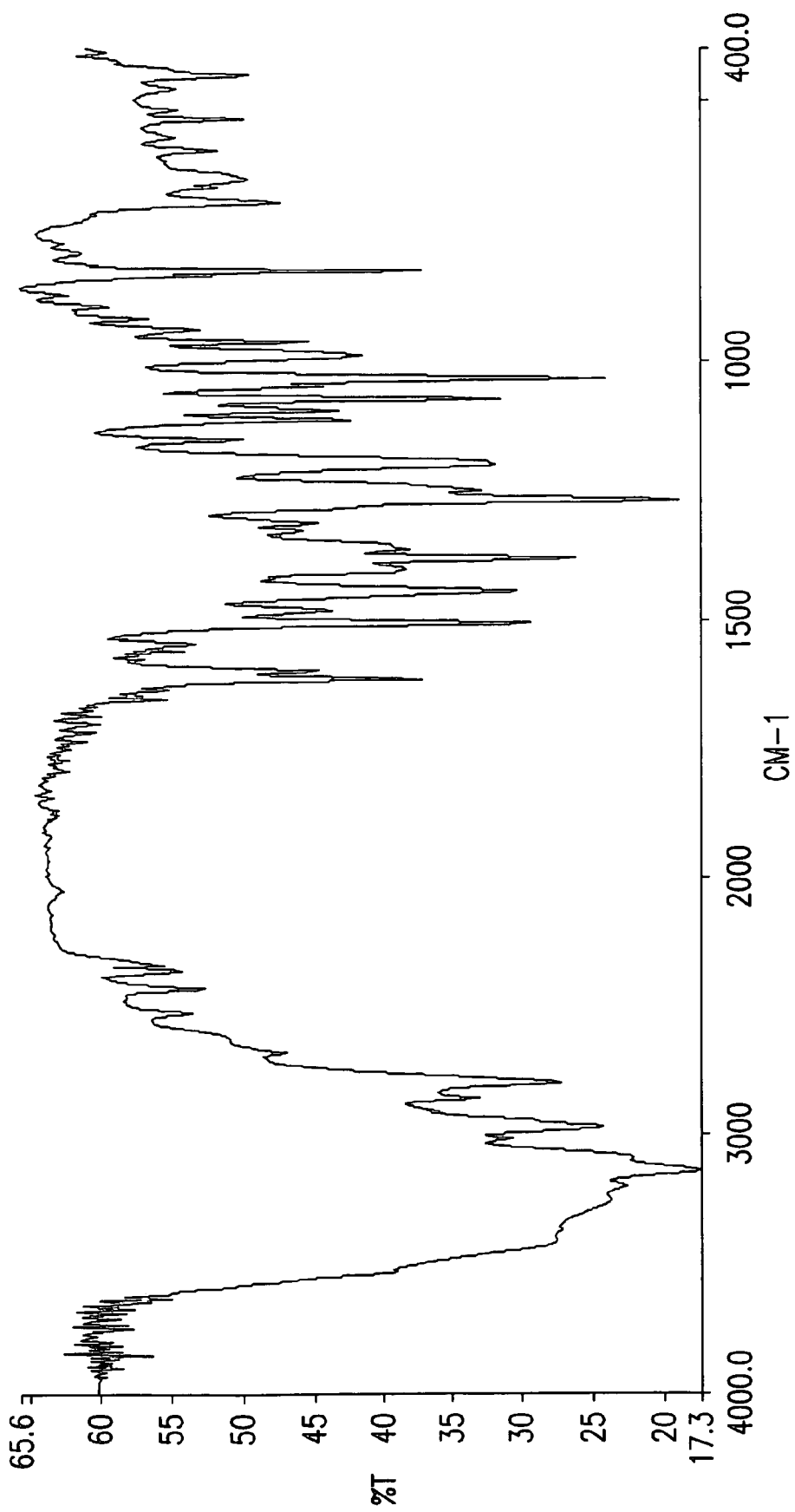
FIG. 3 is a characteristic FT-IR spectrum of levalbuterol HCl Polymorph B.

One embodiment of the invention encompasses levalbuterol HCl Polymorph B. The invention also encompasses processes for preparing levalbuterol Polymorph B with considerable simplicity and to the novel levalbuterol HCl Polymorph B obtained by using this process.

The present invention relates to the solid state physical properties of levalbuterol HCl. These properties can be influenced by controlling the conditions under which levalbuterol HCl is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. These conformational and orientational factors in turn result in particular intramolecular interactions and intermolecular interactions with adjacent molecules that influence the macroscopic properties of the bulk compound. A particular polymorphic form may give rise to distinct spectroscopic properties that may be detectable by powder X-ray diffraction, solid state 13C NMR spectrometry and infrared spectrometry. The polymorphic form may also give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others.

As used herein, the term: "(R)-SLB(D)-DBTA" refers to R enantiomer of albuterol D-DBTA complex.

In one embodiment the invention encompasses processes for preparing levalbuterol HCl Polymorph B which comprise suspending or forming a slurry of (R)-SLB.D-DBTA in at least one organic solvent; adding HCl with a $C_1$-$C_4$ alcohol to the suspension or slurry of the solid SLB.D-DBTA until levalbuterol HCl Polymorph B is obtained; and isolating the levalbuterol HCl Polymorph B. Not to be limited by theory, it is believed that the process occurs by a solid to solid transformation.

The organic solvent includes, but is not limited to, at least one linear or branched $C_3$-$C_{10}$ ester, linear or branched $C_3$-$C_{10}$ ketone, linear or branched $C_3$-$C_{10}$ ether, $C_6$-$C_{10}$ aromatic hydrocarbon, linear or branched $C_1$-$C_4$ alcohol, dimethylsulfoxide, dimethylformamide, acetonitrile, or dichloromethane. Optionally, water is added to the solvent. Preferably, the solvent includes, but is not limited to, at least one of ethylacetate, acetone, tetrahydrofuran, dimethylcarbonate, acetonitrile, toluene, xylene, methanol, ethanol, isopropanol, dimethylsulfoxide, or dimethylformamide. More preferably, the solvent is ethylacetate. Preferably, the ratio of the organic solvent to the $C_1$-$C_4$ alcohol, which is added with the HCl, is about 90% to about 10% by volume, more preferably, the ratio of solvents is about 95% to about 5% by volume, and most preferably, the ratio of solvents is about 95% ethylacetate and about 5% methanol by volume. Preferably, the solvent is present in an amount of about 5 ml/g to about 20 ml/g of the (R)-SLB.D-DBTA.

The reaction may be carried out at temperatures of about −10° C. to about 40° C., preferably the temperature is about room temperature. Alternatively, the slurry may be ooled, preferably at a temperature of about −10° C. to about 10° C., more preferably at about −5° C. to about 5° C., and most preferably at a about −2° C. to about 2° C.

The HCl is added with a $C_1$-$C_4$ alcohol. Preferably, the $C_1$-$C_4$ alcohol is methanol. For example, methods for adding HCl include, but are not limited to, adding aqueous HCl (37%), HCl gas, HCl in methanol, HCl in DMF, or HCl in ethereal solutions. Typically, HCl is added in an amount of about 1.2 equivalents of HCl per equivalent of SLB.D-DBTA.

In another embodiment, the invention encompasses levalbuterol HCl Polymorph B. Polymorph B is characterized using x-ray diffraction by peaks at 8.7, 14.5, 19.0, and 19.6 degree two-theta, ±0.2 degree two-theta. Polymorph B may be further characterized by x-ray diffraction peaks at 20.6, 22.6, 30.9, and 35.0 degree two-theta, ±0.2 degree two-theta. Alternatively, Polymorph B is characterized by infrared peaks at 3137, 2865, 2437, 2364, 1268, and 1071 cm$^{-1}$. Polymorph B may be further characterized by IR peaks at 2970, 2802, 1615, 1599, 1560, 1546, 1507, 1482, 1444, 1364, 1313, 1199, 1151, 1111, 1094, 1034, 992, 829, 697, 653, 597, 537, and 454 cm$^{-1}$. DSC curves of Levalbuterol HCl polymorph form B has an additional small endothermic event in the temperature range of 144° C. to 169° C. and decomposes during melting in the temperature range of 181° C. to 188° C. Additionally, the levalbuterol hydrochloride Polymorph B has an L.O.D. of about 0.1% or 0.6% TGA by weight or a water content of 0.12 to 0.23% by weight.

Table 1 summarizes the loss on drying (LOD) as a percentage of weight over a temperature range, as well as the water content for a sampling of polymorphs.

TABLE 1

TGA and Water Content for Sample Polymorphs.

| Sample | Crystal Form | TGA LOD (%) | TGA Temp (° C.) | LOD (%) | Temp (° C.) | Water Content (%) |
|---|---|---|---|---|---|---|
| 1 | B | 0.04 | 31-100 | 0.33 | 145-159 | 0.14 |
| 2 | B | 0.15 | 31-102 | 0.13 | 133-154 | 0.13 |
| 4 | B | 0.05 | 36-102 | 0.54 | 136-170 | 0.12 |
| 5 | B | 0.03 | 37-103 |  |  | 0.16 |
| 7 | B | 0.06 | 33-102 | 0.42 | 130-150 | 0.23 |
| 9 | B | 0.08 | 51-65 | 0.33 | 153-171 | 0.12 |

Table 2 summarizes the hygroscopicity and crystal structure of a 100% sample of either valbuterol HCl Polymorph A or Polymorph B after each same was individually exposed to different levels of humidity for one week. After each exposure the water content was determined by Thermal Gravimetric Analysis (TGA) and reported as loss on drying (LOD) as a weight percentage and the crystal structure was determined by X-ray Diffraction (XRD). After exposure of each sample up to about 80% relative humidity, it was determined that the water content of Polymorph A was about 0.23 to 0.97 percent and the water content of Polymorph B was about 0.21 to 0.48 percent. After exposure of each sample at about 100% relative humidity for one week, the water content of Polymorph A was about 34 percent and that of Polymorph B was about 36 percent.

TABLE 2

Results of hygroscopicity test of levalbuterol HCl Polymorph B

| RH (%) | LOD (%)[a] (Polymorph B) | Polymorph by XRD[b] (Polymorph B) |
|---|---|---|
| 0 | 0.21 | B |
| 20 | 0.25 | B |
| 40 | 0.25 | B |
| 60 | 0.30 | B + A |
| 80 | 0.48 | A >> B |
| 100 | 36.0 | A |

[a] The water content of each individual sample of Polymorph B after being exposed to the various levels of relative humidity (RH %), equilibrated and analyzed by thermal gravimetric analysis.
[b] The crystal structure of each individual sample of Polymorph B after being exposed to the various levels of relative humidity (RH %) of column one, equilibrated and analyzed by x-ray diffraction.

FIG. 1 illustrates the results in graphical form, which graphs correlate the water content by weight percentage to the increasing levels of relative humidity for a sample of levalbuterol HCl Polymorph A or Polymorph B. After exposure of each sample up to about 80% relative humidity, the water content of each sample was less than about one percent. For each sample after exposure at about 100% relative humidity for one week, the water content of each sample was more than about 30%. Thus, based on the results of Table 3 and FIG. 1, samples of Polymorph A or Polymorph B absorbed sufficient water to dissolve the polymorph after one-week exposure at 100% relative humidity. At higher relative humidities, Polymorph A was detected in samples of Polymorph B. For example, at a relative humidity of 60%, the amount of Polymorph A was greater than the amount of Polymorph B. At 100% relative humidity, only Polymorph A was detected and Polymorph B was not detected at all.

The heat stability of the crystal Polymorph B of levalbuterol HCl was examined using XRD. Samples of 100% Polymorph B that were stored in an oven at 160° C. for about 15 or 30 minutes. After each time interval, a sample was analyzed by XRD. After about 15 minutes, levalbuterol HCl Polymorph A was detected in the sample of Polymorph B.

While the present invention is described with respect to particular examples and preferred embodiments, it is understood that the present invention is not limited to these examples and embodiments. The present invention, as claimed, therefore includes variations from the particular examples and preferred embodiments described herein, as will be apparent to one of skill in the art.

EXAMPLES

The X-Ray diffraction (XRD) analysis was conducted using an ARL X-Ray powder diffractometer (model X'TRA-030) equipped with a Peltier detector, round standard aluminum sample holder with round zero background, and quartz plate. The scanning parameters were from a range of about 2-40 degree two θ (±0.2 degrees) and a continuous scan at a rate of about 3 degrees/min.

Fourier transform infrared (FT-IR) spectroscopy was conducted using a Perkin-Elmer Spectrum 1000 Spectrometer at about 4 cm$^{-1}$ resolution with about 16 scans in the range of 4000-400 cm$^{-1}$. Samples were analyzed in KBr pellet and the instrument was calibrated using an empty cell as a background.

Differential scanning calorimetry (DSC) was conducted using a Mettler Toledo DSC 822$^e$/700 with a sample weight of about 3-5 mg, a heating rate of about 10° C./min., using a 3 holed crucible, under a stream of N$_2$ at a flow rate of about 40 ml/min. The sample was scanned between a range of about 30° C. to about 250° C. at a heating rate of about 10° C./minute.

Thermal Gravimetric Analysis (TGA) was conducted using a Mettler Toledo TGA/SDTA 851$^e$ using a sample weight of about 7-15 mg, a heating rate of about 10° C. min. under a N$_2$ stream at a N$_2$ flow rate of about 50 ml/min. The samples were scanned at a range between about 30° C. to about 250° C.

Example 1

In a 500 ml reactor equipped with a condenser, thermometer, and mechanical stirrer loaded at room temperature and under nitrogen a suspension of wet pure (R)-SLB.(D)-DBTA (39.73 g wet, 30 g at 100%; 0.05 moles), in ethylacetate (331 ml) was formed. The suspension was cooled to 0° C.±2° C., the temperature was maintained, and in about 5 minutes HCl (37%, 5.89 g, 0.06 moles, 1.2 eq. in MeOH 18 ml) was added. The suspension was stirred at 0° C.±2° C. for 1 hour, the solid was collected by filtration, and washed with ethylacetate (3×10 ml). The wet solid (18.1 g) was suspended in an ethylacetate and methanol mixture (90 ml, 90:10 v/v) and the suspension was stirred at 20° C. to 25° C. for 4 hrs. The solid was collected by filtration and washed with ethylacetate to obtain levalbuterol HCl polymorph B (12.9 g dry weight, 94%).

Example 2

In a 250 ml reactor equipped with a condenser, thermometer, and mechanical stirrer loaded at room temperature and under nitrogen a suspension of wet pure (R)-SLB.(D)-DBTA (20 g, 0.0335 moles) and ethylacetate (150 ml). The suspension was cooled at 7° C. to 8° C., the temperature was maintained, and in about 3 minutes HCl (34%, 3.6 g, 0.0335 moles, 1 eq. in MeOH) and ethylacetate (10 ml) were added. The suspension was warmed to 15° C. to 20° C. and after 1 hour, the solid was collected by filtration, and washed with ethylacetate (3×10 ml), and the solid was collected by filtration. Levalbuterol Polymorph B was collected (8.68 g).

Example 3

Table 3 also summarizes the results following example 18 of CN 1273966 and example 7 of WO 95/32178, as illustrated in Examples 1-5.

TABLE 1

Results of different reaction and slurry solvents

| No | Solvent/Temp/Time | Conditions | Xtal Form | DSC (° C., J/g) |
|---|---|---|---|---|
| 1[a] | Lvl base in EtOH + HCl in Et$_2$O + Et$_2$O | According to CN 1273966 example 18 | A | 178 (139) |
| 2[b] | Xtl. sample 1 from EtOH-MTBE | According to CN 1273966 example 18 | A | 189 (155) |
| 3[a] | Lvl base in EtOH + HCl in Et$_2$O + MTBE | According to WO 95/32178 example 7 | A | 199 (47) |
| 4[b] | Xtl. sample 3 from EtOH-MTBE | According to WO 95/32178 example 7 | A | 196 (146) |
| 5[b] | Xtl. sample 3 from EtOH-MTBE | According to CN 1273966 example 19 | A | 194 (131) |

[a] The starting material was a crude sample of levalbuterol base.
[b] The starting material was a purified sample of levalbuterol HCl A.

What is claimed is:

1. A crystalline polymorph of Levalbuterol hydrochloride, Form B, characterized by
X-ray diffraction peaks at 8.7, 14.5, 19.0, and 19.6 degree two-theta, ±0.2 degree two-theta.

2. The crystalline polymorph of levalbuterol hydrochloride Form B according to claim 1 further characterized by x-ray diffraction peaks at 20.6, 22.6, 30.9, and 35.0 degree two-theta, ±0.2 degree two-theta.

3. The crystalline polymorph of levalbuterol hydrochloride Form B according to claim 1 further characterized by IR peaks at 2970, 2802, 1615, 1599, 1560, 1546, 1507, 1482, 1444, 1364, 1313, 1199, 1151, 1111, 1094, 1034, 992, 829, 697, 653, 597, 537, and 454 $cm^{-1}$.

4. A process for preparing levalbuterol hydrochloride Polymorph B characterized by X-ray diffraction peaks at 8.7, 14.5, 19.0, and 19.6 degree two-theta, ±0.2 degree two-theta, said process comprising:
suspending or forming a slurry of the R enantiomer of albuterol dibenzoyl tartrate complex in at least one solvent;
adding hydrogen chloride in a $C_1$-$C_4$ alcohol to the suspension or slurry until levalbuterol hydrochloride Polymorph B is obtained; and
isolating the levalbuterol hydrochloride Polymorph B;
wherein the at least one solvent includes at least one linear or branched $C_3$-$C_{10}$ ester, linear or branched $C_3$-$C_{10}$ ketone, linear or branched $C_3$-$C_{10}$ ether, $C_6$-$C_{10}$ aromatic hydrocarbon, linear or branched $C_1$-$C_4$ alcohol, dimethylsulfoxide, dimethylformamide, acetonitrile or dichloromethane.

5. The process according to claim 4 further comprising adding water to the organic solvent.

6. The process according to claim 4, wherein the solvent includes at least one of ethyl acetate, acetone, tetrahydrofuran, dimethylcarbonate, acetomtrile, toluene, xylene, methanol, ethanol, isopropanol, dimethylsulfoxide, or dimethylformamide.

7. The process according to claim 4, wherein the ratio of the organic solvent to the $C_1$-$C_4$ alcohol, which is added with the HCl, is about 90% to about 10% by volume.

8. The process according to claim 7, wherein the ratio of the organic solvent to the $C_1$-$C_4$ alcohol, which is added with the hydrogen chloride, is about 95% to about 5% by volume.

9. The process according to claim 7 or 8, wherein the organic solvent is ethyl acetate and the $C_1$-$C_4$ alcohol is methanol in a ratio of about 95% to about 5% by volume.

10. The process according to claim 4, wherein the reaction is carried out at temperature of about −10° C. to about 40° C.

11. The process according to claim 4, wherein the reaction is carried out at room temperature.

12. The process according to claim 4, wherein the hydrogen chloride is added as a solution or a gas in a $C_1$-$C_4$ alcohol.

13. The process according to claim 4, wherein the hydrogen chloride is added in an amount of about 1.2 equivalents of hydrogen chloride per equivalent of the R enantiomer of albuterol dibenzoyl tartrate complex.

14. The crystalline polymorph of levalbuterol hydrochloride Form B according to claim 1 further characterized by differential scanning calorimetry curves of small endothermic event in the temperature range of 144° C. to 169° C. and decomposition during melting in the temperature range of 181° C. to 188° C.

15. The crystalline polymorph of levalbuterol hydrochloride Form B according to claim 3 further characterized by infrared peaks at 3137, 2865, 2437, 2364, 1268, and 1071 $cm^{-1}$.

* * * * *

UNITED STATES PATENT AND TRADEMARK OFFICE
CERTIFICATE OF CORRECTION

PATENT NO. : 7,488,758 B2
APPLICATION NO. : 11/133722
DATED : February 10, 2009
INVENTOR(S) : Merli et al.

It is certified that error appears in the above-identified patent and that said Letters Patent is hereby corrected as shown below:

Column 8
Line 1, change "acetomtrile" to --acetonitrile--

Signed and Sealed this

Thirteenth Day of October, 2009

David J. Kappos
*Director of the United States Patent and Trademark Office*